United States Patent
Abraham-Fuchs et al.

(10) Patent No.: US 8,955,366 B2
(45) Date of Patent: Feb. 17, 2015

(54) MULTIFUNCTIONAL CONTROL VALVE FOR GAS MEASUREMENT INSTRUMENTS

(75) Inventors: Klaus Abraham-Fuchs, Erlangen (DE); Maximilian Fleischer, Höhenkirchen (DE); Karsten Hiltawsky, Schwerte (DE); Oliver Hornung, Fürth (DE); Thomas Krüger-Sundhaus, Pommersfelden (DE); Erhard Magori, Feldkirchen (DE); Peter Paulicka, Röttenbach (DE); Roland Pohle, Ottenhofen (DE); Oliver Von Sicard, München (DE)

(73) Assignee: Siemens Aktiengesellschaft, Munich (DE)

( * ) Notice: Subject to any disclaimer, the term of this patent is extended or adjusted under 35 U.S.C. 154(b) by 1119 days.

(21) Appl. No.: 12/890,991

(22) Filed: Sep. 27, 2010

(65) Prior Publication Data

US 2011/0072883 A1 Mar. 31, 2011

(30) Foreign Application Priority Data

Sep. 28, 2009 (DE) .......... 10 2009 043 236

(51) Int. Cl.
*G01N 1/22* (2006.01)
*G01N 7/00* (2006.01)
(Continued)

(52) U.S. Cl.
CPC .............. *A61B 5/097* (2013.01); *G01N 33/497* (2013.01)
USPC .......................................... 73/23.3; 73/31.05

(58) Field of Classification Search
CPC ............ G01N 33/497; G01N 33/0031; G01N 33/4972; G01N 2033/4977; G01N 2033/4975; G01N 33/0009; G01N 33/0022; G01N 35/1097; G01N 33/0011; G01N 33/0013; A61B 5/097; A61B 5/087; B60W 2540/02
USPC .............. 73/23.2, 23.3, 31.05, 23.31, 863.73, 73/863.41, 863.11, 863.12, 863.21, 73/863.23, 863.31, 863.33, 863.45, 863.71
See application file for complete search history.

(56) References Cited

U.S. PATENT DOCUMENTS 3,622,278 A * 11/1971 Elzinga et al. ................ 436/181
4,799,374 A * 1/1989 Bossart et al. ................ 250/343
(Continued)

FOREIGN PATENT DOCUMENTS

DE 10158288 A1 5/2003
DE 202008007748 U1 9/2008

OTHER PUBLICATIONS

B. Buszewski et al: "Human exhaled air analytics: biomarkers of diseases", Biomedical Chromatography, Jun. 21, 2007 (6), 533-66; Others; 2007.
(Continued)

*Primary Examiner* — Daniel S Larkin
*Assistant Examiner* — Jamar Ray
(74) *Attorney, Agent, or Firm* — Harness, Dickey & Pierce P.L.C.

(57) ABSTRACT

A multifunctional control valve for gas measurement instruments, e.g., for respiratory gas analysis, is disclosed. In at least one embodiment, the multifunctional control valve includes a first inlet opening, an outlet opening, a main line, and a bypass line, wherein a measurement chamber is in the main line, wherein the measurement chamber is arranged downstream of a first multiway valve which can selectively connect the main line or the bypass line with the inlet opening, and wherein the measurement chamber is arranged upstream of a second multiway valve which can selectively connect the main line or the bypass line with the outlet opening.

16 Claims, 2 Drawing Sheets

(51) Int. Cl.
*A61B 5/097* (2006.01)
*G01N 33/497* (2006.01)

(56) References Cited

U.S. PATENT DOCUMENTS

| | | | | |
|---|---|---|---|---|
| 5,022,406 | A * | 6/1991 | Tomlinson | 600/532 |
| 5,929,318 | A * | 7/1999 | Smith | 73/23.2 |
| 6,345,545 | B1 * | 2/2002 | Linker et al. | 73/863.23 |
| 7,279,132 | B2 * | 10/2007 | Sultan et al. | 422/83 |
| 8,163,149 | B2 * | 4/2012 | Stromereder et al. | 204/431 |
| 2004/0177673 | A1 * | 9/2004 | Mottram et al. | 73/23.2 |
| 2007/0051163 | A1 * | 3/2007 | Wohltjen | 73/31.07 |
| 2008/0163674 | A1 * | 7/2008 | Bonne et al. | 73/31.05 |
| 2010/0081955 | A1 * | 4/2010 | Wood et al. | 600/532 |
| 2011/0001625 | A1 * | 1/2011 | Reilly et al. | 340/632 |
| 2012/0150055 | A1 * | 6/2012 | Carlson et al. | 600/532 |
| 2012/0165694 | A1 * | 6/2012 | Meka et al. | 600/532 |

OTHER PUBLICATIONS

Pleil: "Role of exhaled breath biomarkers in environmental health science" Journal of Toxicology and Environmental Health, Part B, 11; 613-629, 2008; Others; 2008.

* cited by examiner though in the area of the outlet opening the one-way valve must have the opposite direction of opening to the one-way valves in the area of the inlet openings.

MULTIFUNCTIONAL CONTROL VALVE FOR GAS MEASUREMENT INSTRUMENTS

PRIORITY STATEMENT

The present application hereby claims priority under 35 U.S.C. §119 on German patent application number DE 10 2009 043 236.1 filed Sep. 28, 2009, the entire contents of which are hereby incorporated herein by reference.

FIELD

At least one embodiment of the present invention generally relates to a multifunctional control valve for gas measurement instruments, e.g., for respiratory gas analysis.

BACKGROUND

Instruments for respiratory gas analysis for medical diagnostics or lifestyle uses are increasingly common on the market. Particularly the development of inexpensive, selective, and highly sensitive sensors makes possible the development of small, portable, and inexpensive instruments in the future.

There are a multiplicity of biomarkers, metabolic products, and other substances which can be measured in respiratory gas and can provide information about inflammatory diseases, cancers, metabolic diseases, or poisoning symptoms of the patient; see, for example, Pleil in J Toxicol Environ Health B Crit. Rev. 2008 October; 11(8): 613-29. Role of exhaled breath biomarkers in environmental health science or Buszewski et al, Human exhaled air analytics: biomarkers of diseases, Biomed Chromatogr. 2007 June; 21(6): 553-66. Review. In practice, respiratory gas analysis is already used in the diagnosis of poisonings, asthma, diabetes, lung cancer, inflammatory respiratory diseases, and kidney or liver failure.

The analysis of respiratory gas can provide information about many metabolic processes of the human body. It is thus possible, for example, to infer the alcohol content of the blood, to diagnose an infection of the gastrointestinal tract with *Heliobacter pylori* bacteria, or to deduce the gestation cycle of a woman from the profile of the $CO_2$ content.

To check the training efficiency of athletes, it can be helpful to measure the acetone content of the respiratory air. It is very helpful to monitor the NO content of the respiratory air to improve disease management of asthma patients.

In respiratory gas analysis, it is, however, important in most cases for the clinical value of the measured result that the correct portion of the volume exhaled is measured. The first portion of the air of an exhalation process comes from the oral and pharyngeal cavities and also the upper bronchi, the middle portion comes from the bronchi and bronchioles, the last portion ("end-expiratory") in particular from the alveoli. Thus, for example, it is important for the diagnosis of the inflammatory reaction of asthma patients to measure the middle portion of the volume exhaled.

For an optimized measurement instrument for respiratory gas analysis, it is therefore necessary to have an apparatus and a method for controlling the patient's respiratory flow through the measurement instrument such that really the clinical important portion of the respiratory volume is conducted over the measurement sensor and, at the same time, the patient can breathe as naturally as possible. An unnatural breathing process (e.g., against too high an air resistance, or an abrupt termination of the expiration by the valve closure) would be, firstly, uncomfortable for the patient when using the instrument and could, secondly, distort the desired measured result. The technical solution for this depends crucially on whether the gas sensor has to operate in a continuous gas flow, or in a standing volume of a closed chamber.

Existing systems for NO analysis of respiratory gas measure in a continuous flow due to the widely used sensor principle. The routing of gas flow, which is used in these instruments, is less suitable for measurement in a sealed measurement chamber.

SUMMARY

In at least one embodiment an optimized solution for measurement in a sealed measurement chamber is proposed.

At least one embodiment of the invention relates to an apparatus and at least one embodiment relates to a method. Further aspects of at least one embodiment of the present invention relate to the following, numbered paragraphs:

1. An apparatus for respiratory gas analysis, comprising: a first inlet opening, an outlet opening, a main line, and a bypass line, wherein a measurement chamber is in the main line, and wherein the measurement chamber is located after a first multiway valve which can selectively connect the main line or the bypass line with the inlet opening, and wherein the measurement chamber is located before a second multiway valve which can selectively connect the main line or the bypass line with the outlet opening.
2. The apparatus as claimed in paragraph 1, wherein the measurement chamber can be insulated from the ambient air by the first and second multiway valves.
3. The apparatus as claimed in either one of the preceding paragraphs, wherein the first and/or second multiway valve is a rotatable valve.
4. The apparatus as claimed in any one of the preceding paragraphs, wherein the first and/or second multiway valve can be set such that, before and/or after the measurement chamber, a gas-conditioning device can be introduced into the flow path.
5. The apparatus as claimed in paragraph 4, wherein the gas-conditioning device is selected from the group comprising filter, activated carbon filter, catalyst, oxidant, and desiccant, or combinations thereof.
6. The apparatus as claimed in paragraph 4 or 5, wherein the gas-conditioning device is integral to the first and/or second multiway valve.
7. The apparatus as claimed in any one of the preceding paragraphs, comprising additionally a second inlet opening.
8. The apparatus as claimed in any one of the preceding paragraphs, comprising additionally a pump which can pump ambient air into the measurement chamber from the first or second inlet opening or, opposite to the direction of flow present in the measurement process, from the outlet opening.
9. The apparatus as claimed in paragraph 7 or 8, wherein the gas-conditioning device as claimed in paragraph 4 or a further gas-conditioning device is arranged in the flow path between the second inlet opening and the measurement chamber.
10. The apparatus as claimed in any one of the preceding paragraphs, wherein a flow measurement apparatus for determining the flow rate or a gas volume is arranged in the flow path between first inlet opening and outlet opening.
11. The apparatus as claimed in any one of the preceding paragraphs, wherein at least one one-way valve is arranged in the flow path between first inlet opening and outlet opening.
12. The apparatus as claimed in paragraph 11, wherein the at least one one-way valve is arranged between the first inlet opening and the measurement chamber and/or between the second inlet opening and the measurement chamber and/or between the measurement chamber and/or the outlet opening.

13. The apparatus as claimed in any one of the preceding claims, wherein a heating apparatus is assigned to the measurement chamber.

At least one embodiment of the invention further relates to the method of the following numbered paragraphs:

14. A method for operating an apparatus for respiratory gas analysis according to any one of paragraphs 1 to 13, comprising the following steps:

conducting the respiratory air from a first inlet opening of the apparatus through a bypass line to an outlet opening, conducting the expiratory air from a first inlet opening of the apparatus into a measurement chamber upon reaching a respiratory gas fraction to be measured of expiratory air of a test person, insulating the measurement chamber from the ambient air and measuring a gas analyte and diverting further expiratory air from the first inlet opening of the apparatus through the bypass line to the outlet opening.

15. The method as claimed in paragraph 14, comprising additionally the flushing of the measurement chamber with ambient air.

At least one embodiment of the invention has at least one of the following features and advantages:

A system comprising a first and a second multiway valve, which is switchable by means of mechanical movement, for example by rotation, between at least 3 functional positions, wherein the first multiway valve is positioned at the entrance of the measurement chamber such that it can be connected, when required, in a selectable functional position with the measurement chamber.

A system comprising a first and a second multiway valve, which is switchable by means of mechanical movement, for example by rotation, between, for example, 3 functional positions, wherein the first and second multiway valves are positioned at the entrance and the exit of the measurement chamber, respectively, such that, when required, the main line with the measurement chamber can be connected in a selectable functional position with at least the first inlet opening and the outlet opening, or, in a second functional position, the bypass line can be connected with at least the first inlet opening and the outlet opening.

A system comprising a first and a second multiway valve with at least one gas-conditioning device, which valves are switchable, independently of one another, by means of mechanical movement, for example by rotation, so that, when required, the at least one gas-conditioning device can be connected with the measurement chamber for the flow path of the gas to pass through the gas-conditioning device.

In an embodiment of the invention, the multiway valves can comprise gas flow channels of different geometries.

In an embodiment of the invention, a gas-conditioning device can be arranged in a gas flow channel in a multiway valve.

A gas-conditioning device can fulfill the following functions: filtering the gas stream (for example, by way of activated carbon or a particle filter), dehumidifying the gas (for example, by way of silica gel, water-binding salts, e.g., copper sulfate or the like), converting the gas (such as, for example, oxidation of an analyte, e.g., NO to $NO_2$ by means of an oxidant or by means of a catalyst).

The oxidant can be, for example, potassium permanganate, perchlorate salts, or other useful oxidants. The catalyst can be, for example, noble metal catalysts, metal oxide catalysts, or photocatalysts.

Instead of a gas-conditioning device, a device for temperature measurement or gas flow measurement can also be included in the flow path.

Preferably, a functional position can be set in which sensitive components in the control valve and/or the measurement chamber are insulated from the external air, and therefore, in the inoperative state, no damaging influences from outside can act.

The valves can be further brought into a functional position in which the measurement chamber can be cleaned with a gas stream, where the gas stream can be cleaned external air and cleaning can be carried out with the aid of, for example, air flow through activated carbon.

In addition, a pump can also be included. This pump can also be implemented as a fan.

A gas mixture of defined composition can also be used in this mode for calibrating and/or checking the sensor.

This gas mixture for calibration can comprise the analyte to be detected, for example, at a defined concentration. However, it can also be free of the analyte to be detected (zero air). The gas mixture for calibration can be stockpiled in a container intended for this purpose (e.g., gas cartridge).

In an embodiment, the gas-conditioning devices, temperature sensors and flow sensors, and/or the gas sensor of the measurement chamber are arranged such that they can be externally accessed and exchanged. This, for example, makes sense for an exhaustible gas-conditioning device, such as a potassium permanganate gas converter which has to be replaced after one or more usage cycles.

BRIEF DESCRIPTION OF THE DRAWINGS

Embodiments of the invention will now be described with reference to FIGS. 1 to 6 below, showing.

DETAILED DESCRIPTION OF THE EXAMPLE EMBODIMENTS

Figure 1:
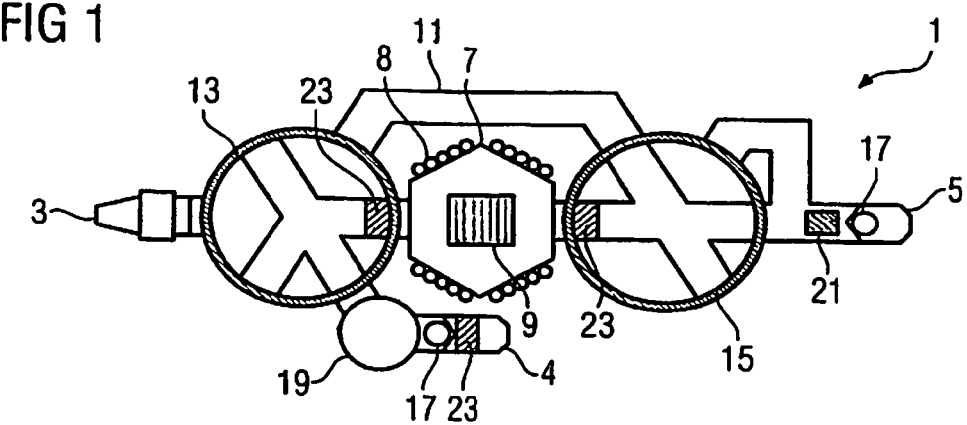
FIG. 1: An embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows, by way of example, an embodiment of the apparatus 1 according to the invention with a first inlet opening 3, which is the mouthpiece, a second inlet opening 4, and an outlet opening 5. A measurement chamber 7 with a temperature control device 8 and a gas sensor 9 are arranged between the first multiway valve 13 and the second multiway valve 15. A bypass line 11 is likewise arranged in a main line 2 between the first multiway valve 13 and the second multiway valve 15 such that, when required, the main line 2 with the measurement chamber 7 can be connected in a selectable functional position with at least the first inlet opening 3 and the outlet opening 5. Upstream of the outlet opening 5 and downstream of the second inlet opening 4, there are arranged one-way valves 17 which are, for example, implemented as a simple nonreturn valve. Downstream of the second inlet opening 4 and in the flow channels of the multiway valves 13, 15, gas-conditioning devices 23 can be included. These devices can be, for example, activated carbon filters, desiccants, and/or oxidants. Upstream of the outlet opening 5, a flow sensor 21 is included. A pump 19 can pump ambient air into the measurement chamber 7 from the first inlet opening 3 or second inlet opening 4 or, opposite to the direction of flow present in the measurement process, from the outlet opening.

The position shown in FIG. 1 of the multiway valves 13, 15 can, for example, be used when the instrument is not in use.

Figure 2:
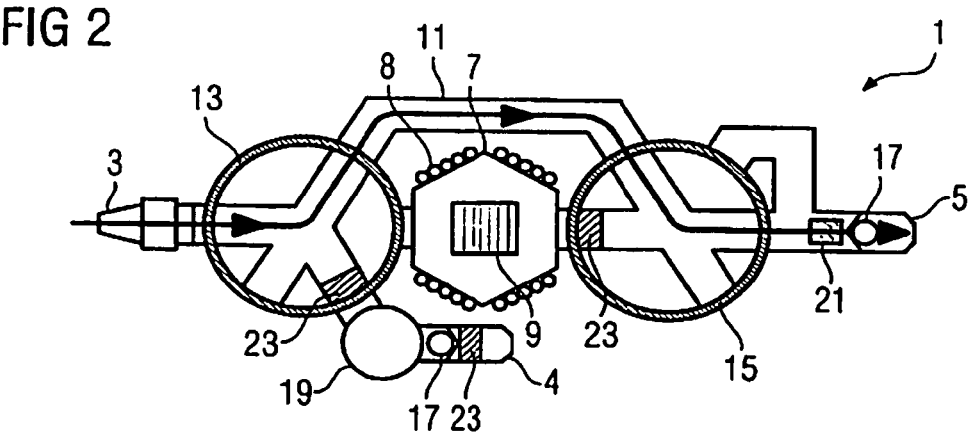
FIG. 2: The embodiment according to FIG. 1 in a 1st functional position.

FIG. 2 shows the embodiment according to FIG. 1 in a 1st functional position: The multiway valves 13, 15 are set such that the flow path runs from the mouthpiece 3 through the bypass line 11 to the outlet opening 5. This position is selected at the beginning of a measurement process, and the test person/patient has to exhale through the mouth here.

Figure 3:
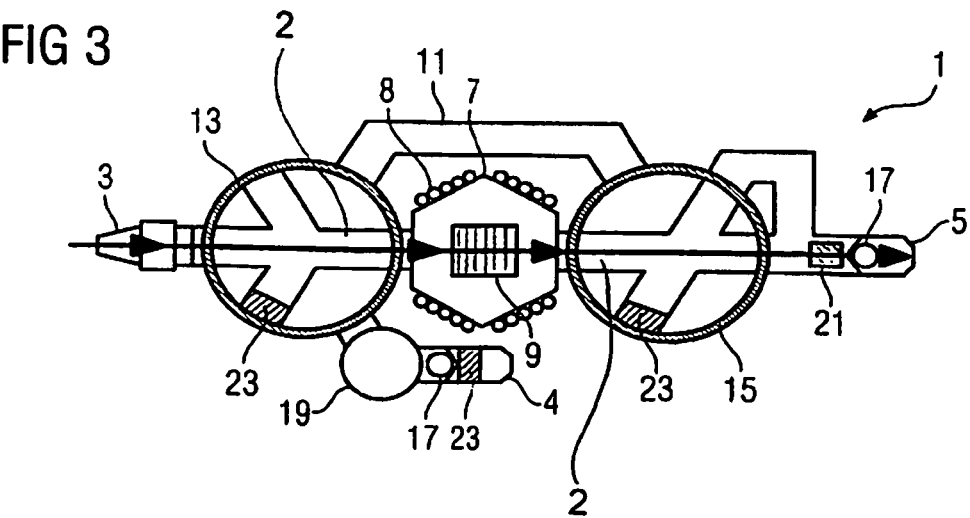
FIG. 3: The embodiment according to FIG. 1 in a 2nd functional position.

FIG. 3 shows the embodiment according to FIG. 1 in a 2nd functional position: The multiway valves 13, 15 are set such that the flow path runs from the mouthpiece 3 through the measurement chamber 7 to the outlet opening 5. This position is selected during the measurement process when the expiration fraction which is to be measured has been reached, for example the middle or the end-expiratory fraction, in order to fill the measurement chamber with expiratory air. Reaching the desired fraction is indicated by, for example, the flow sensor 21 or determined after a defined period of time (e.g., 1 s, 2 s, 5 s, 10 s), whereupon the position of the multiway valves 13, 15 is switched from the 1st to the 2nd functional position via, for example, an automatic control.

Figure 4:
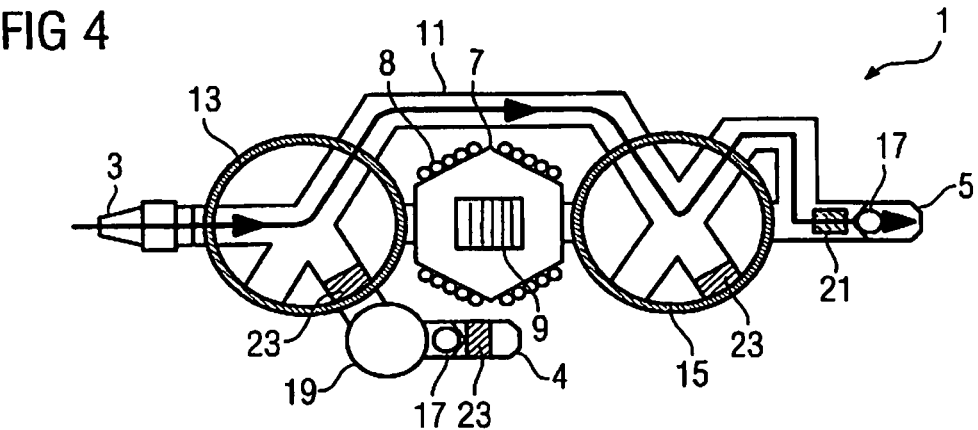
FIG. 4: The embodiment according to FIG. 1 in a 3rd functional position.

FIG. 4 shows the embodiment according to FIG. 1 in a 3rd functional position: The multiway valves 13, 15 are set such that the flow path runs from the mouthpiece 3 through the bypass line 11 to the outlet opening 5 while the measurement chamber is isolated. This position is selected during the measurement process.

Figure 5:
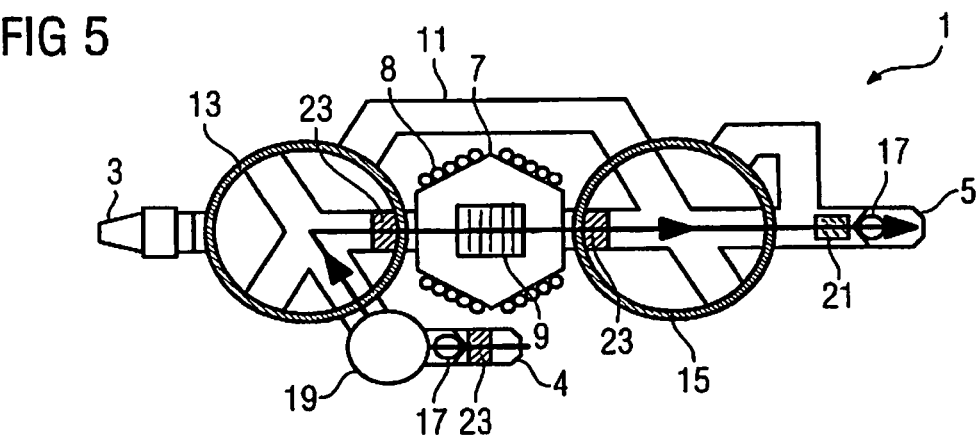
FIG. 5: The embodiment according to FIG. 1 in a 4th functional position.

FIG. 5 shows the embodiment according to FIG. 1 in a 4th functional position: The multiway valves 13, 15 are set such that the flow path runs from the second inlet opening 4 through the gas-conditioning devices 23 through the measurement chamber 7 to the outlet opening 5. This 4th functional position is selected for flushing the measurement chamber after the measurement process.

Figure 6:
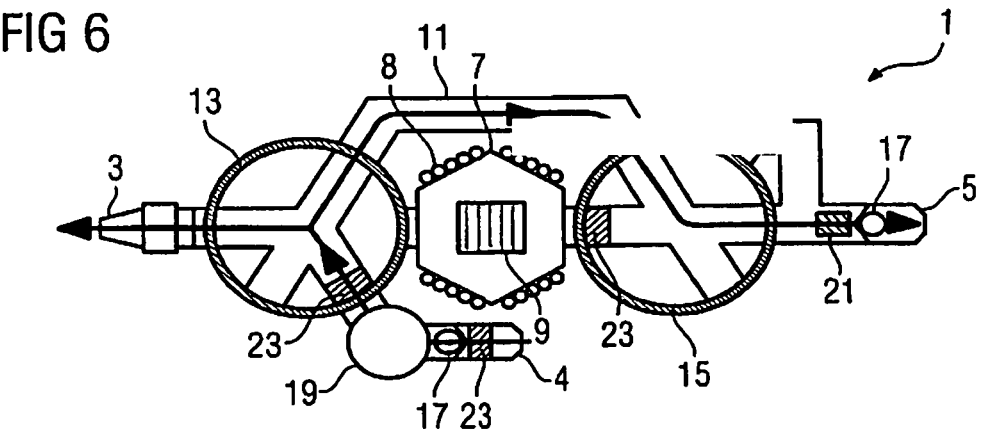
FIG. 6: The embodiment according to FIG. 1 in a 5th functional position.

FIG. 6 shows the embodiment according to FIG. 1 in a 5th functional position: The multiway valves 13, 15 are set such that the flow path runs from the second inlet opening 4 through the gas-conditioning devices 23 through the bypass line 11 to the outlet opening 5 and—in counterflow—through the mouthpiece 3. This 5th functional position is selected for flushing the bypass line 11 and the mouthpiece 3 after the measurement process.

Table 1 below displays an exemplary sequence of events in a measurement process:

| Step | t (s) | v (ml/s) | Valve position | T (° C.) Chamber | T (° C.) Sensor | Flow sensor | Pump | Remark |
|---|---|---|---|---|---|---|---|---|
| Starting position | 0 | 0 | As in FIG. 1 | 20 | 20 | 0 | 0 | |
| Measurement preparation | 0-6 | 50 | As in FIG. 2 | 20 | 20 | 1 | 0 | Expiration |
| Sample acquisition | 7-12 | 50 | As in FIG. 3 | 20 | 20 | 1 | 0 | Expiration |
| Measurement | 13-180 | Variable | As in FIG. 4 | 90 | 130 | 0 | 0 | |
| Flushing the chamber | 181-240 | 0 | As in FIG. 5 | 90 | 130 | 1 | 1 | Regeneration |
| Flushing the lines | 241-300 | 0 | As in FIG. 6 | 20 | 20 | 0 | 1 | Flushing |

In the expiration process, the patient exhales at about 50 ml/s. After the sample acquisition, the measurement chamber is closed, heated by means of a heating apparatus, and the measurement is carried out. Subsequently, the chamber and the lines can be flushed with, for example, filtered ambient air.

The apparatus according to at least one embodiment of the invention makes it possible to have a compact instrument which can be adapted to the requirements of the particular analyte to be detected.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A respiratory gas analyzer, comprising:
   a first inlet opening, the first inlet opening being a mouthpiece of the respiratory gas analyzer;
   an outlet opening;
   a first flow path, the first flow path being a mainline;
   a second flow path, the second flow path being a bypass line that bypasses the first flow path;
   a measurement chamber in the main line;
   a first multiway valve switchable between at least three functional positions to selectively connect the first flow path or the bypass line with the inlet opening; and
   a second multiway valve switchable between at least three functional positions to selectively connect the first flow path or the bypass line with the outlet opening, wherein the measurement chamber is arranged downstream of the first multiway valve and upstream of the second multiway valve.

2. The respiratory gas analyzer as claimed in claim 1, wherein the measurement chamber is insulatable from the ambient air by the first and second multiway valves.

3. The respiratory gas analyzer as claimed in claim 2, wherein at least one of the first and second multiway valve is a rotatable valve.

4. The respiratory gas analyzer as claimed in claim 1, wherein at least one of the first and second multiway valves are rotatable valves.

5. The respiratory gas analyzer as claimed in claim 1, wherein at least one of the first and second multiway valve is settable such that, at least one of upstream of and downstream of the measurement chamber, a gas-conditioning device is introducible into the first flow path.

6. The respiratory gas analyzer as claimed in claim 5, wherein the gas-conditioning device includes at least one of filter, activated carbon filter, catalyst, oxidant, and desiccant.

7. The respiratory gas analyzer as claimed in claim 6, wherein the gas-conditioning device is designed to be an integral part of at least one of the first and second multiway valve or channels thereof.

8. The respiratory gas analyzer as claimed in claim 5, wherein the gas-conditioning device is designed to be an integral part of at least one of the first and second multiway valve or channels thereof.

9. The respiratory gas analyzer as claimed in claim 5, further comprising a second inlet opening.

10. The respiratory gas analyzer as claimed in claim 9, wherein the gas-conditioning device or a further gas-conditioning device is arranged in the first flow path between the second inlet opening and the measurement chamber.

11. The respiratory gas analyzer as claimed in claim 9, wherein at least one one-way valve is arranged in the first flow path between first inlet opening and outlet opening.

12. The respiratory as analyzer as claimed in claim 11, wherein the at least one one-way valve is arranged between at least one of
- the first inlet opening and the measurement chamber;
- the second inlet opening and the measurement chamber; and
- the measurement chamber and the outlet opening.

13. The respiratory gas analyzer as claimed in claim 1, further comprising:
- a pump to pump ambient air into the measurement chamber from the first or second inlet opening or, opposite to the direction of flow present in the measurement process, from the outlet opening.

14. The respiratory gas analyzer as claimed in claim 1, wherein a flow measurement apparatus for determining the flow rate or a gas volume is arranged in the first flow path between first inlet opening and outlet opening.

15. The respiratory gas analyzer as claimed in claim 1, wherein a heating apparatus is assigned to the measurement chamber.

16. The respiratory gas analyzer as claimed in claim 1, wherein at least one one-way valve is arranged in the first flow path between first inlet opening and outlet opening.

\* \* \* \* \*